United States Patent [19]

Tanaka et al.

[11] Patent Number: 5,274,018
[45] Date of Patent: Dec. 28, 1993

[54] SALT TOLERANT SUPER ABSORBENTS

[75] Inventors: Toyoichi Tanaka, Wellesley; Yong-Qing Zhang, Cambridge, both of Mass.

[73] Assignee: Massachusetts Institute of Technology, Cambridge, Mass.

[21] Appl. No.: 705,463

[22] Filed: May 24, 1991

[51] Int. Cl.$^5$ .......................... C08K 5/41; C08L 77/06
[52] U.S. Cl. .................. 524/166; 524/236; 524/599; 524/602
[58] Field of Search ............... 524/166, 236, 599, 602

[56] References Cited

U.S. PATENT DOCUMENTS 4,535,098  8/1985  Evani et al. .................. 524/560

Primary Examiner—Joseph L. Schofer
Assistant Examiner—Jeffrey T. Smith
Attorney, Agent, or Firm—Pennie & Edmonds

[57] ABSTRACT

The invention relates to a novel absorbent composition and manner of using the same. The absorbent has at least the following two components:
  (a) a swellable hydrophobic polymer being capable of absorbing a quantity of water which is at least about 10 times the dry weight of said polymer; and
  (b) an amount of an ionizable surfactant sufficient to form at least a monolayer of said surfactant about said polymer.

The novel absorbent is substantially tolerant to an aqueous solution having a soluble salt, such as sodium chloride.

23 Claims, 6 Drawing Sheets

CATIONIC gel        ANIONIC gel

ION EXCHANGE   ↓  + Na Cl  ↓

IONS DISAPPEAR ⟶

SALT TOLERANT SUPER ABSORBENTS

This invention was made with government support under contract Number DMR-89-20401 awarded by the National Science Foundation. The government has certain rights in the invention.

BACKGROUND OF THE INVENTION

Ionic gels with the capacity to absorb a thousand times their dry weight in water are widely used for diapers and as water absorbents in medical, chemical, and agricultural applications. The dramatic swelling power of these superabsorbent gels is a result of the electrostatic repulsion between the charges along the polymer chains and of the osmotic pressure of the counter ions. It is known, however, that this swelling power is drastically diminished in salt solutions such as saline, urine, or blood. They are no longer super-absorbents in the presence of such physiologic fluids.

Dissolved salts such as $Na^+$ and $Cl^-$ ions have two effects on ionic gels. They screen the polymer charges and they eliminate the osmotic imbalance due to the presence of counter ions in and out of the gel. Dissolved ions effectively convert an ionic gel into a non-ionic gel whereby the swelling power is lost. This has long been a serious problem in medical polymer technology. We demonstrate general methods and representative compositions that eliminate the screening effect of the dissolved salt.

FIELD OF THE INVENTION

Gels are designed with capabilities of super-absorption and of volume phase transition under physiological conditions. Such gels have wide applications including uses in medicine and ocean technology as actuators, sensors, controlled delivery systems, and super-absorbers. The novel principles and absorbents described here will create or improve such applications. In one specific application, the gels are used to make diapers with a much larger absorption capacity than those presently available. Such diapers will be especially useful for those suffering from incontinence.

SUMMARY OF THE INVENTION

The present invention relates to a super water absorbent substantially tolerant to an aqueous solution containing a soluble salt. This novel absorbent comprises:

(a) a swellable hydrophobic polymer being capable of absorbing a quantity of the aqueous solution which is at least about 10 times the dry weight of said polymer; and (b) an amount of an ionizable surfactant sufficient to form at least a monolayer of said surfactant about said polymer.

The absorbent is capable of retaining its super water absorbing properties and temperature-dependent volume phase transition characteristics when brought into contact with the aqueous solution comprising a soluble salt.

It is preferred that the super water absorbent have temperature-dependent volume phase transition characteristics substantially the same as that which occurs in pure water. Specifically, it is preferred that the transition temperature and a volume change at the transition for the absorbent remain substantially the same whether in a salt containing solution or in pure water.

It is further preferred that the ionizable surfactant be anionic, cationic or combinations thereof. It is further preferred that the surfactant component comprises a nonpolar hydrophobic chain to which is attached a polar hydrophilic group. Examples of such a surfactant is sodium dodecylsulfate and dodecyltrimethyl ammonium bromide. The surfactant is preferably in an amount ranging from about 1 to about 10 percent by dry weight of said polymer. The ionizable surfactant can further comprise crosslinkable groups. Such groups may be crosslinked by exposure to UV light. An example of a surfactant which crosslinks upon exposure to UV light is oleic sulfate, $C_8H_{16} = C_8H_{15}-SO_4Na$.

Examples of the polymer component of the super water absorbent are polyacrylamide, poly (N-isopropylacrylamide), poly(acrylic acid), and poly (N-isopropyl-acrylamide-co-acrylic acid).

The super water absorbent may further comprise a crosslinking agent, such as alkylenebisacrylamide and N,N'-methylene-bisacrylamide. The super water absorbent may be in the form of a partially swollen hydrophilic gel. The polymer component of the super water absorbent may optionally have functional groups comprising crown ethers.

The super water absorbent is capable of retaining its super water absorbing properties and temperature-dependent volume phase transition characteristics when brought into contact with an aqueous solution containing up to about 0.15M, about 0.5M or about 1.0M sodium chloride.

This invention provides an improved article that may be used in diapers, napkins, gauzes, tampons, controlled drug delivery systems, sensors, actuators, cathartics, gut diuretic agents, and food bulking agents by providing a water absorbent material comprising:

(a) a swellable hydrophobic polymer being capable of absorbing a quantity of water which is at least about 10 times the dry weight of said polymer; and (b) an amount of an ionizable surfactant sufficient to form at least a monolayer of said surfactant about said polymer.

This invention further provides a method of using the super water absorbent in a combination with antibiotics.

This invention further provides a method of absorbing water from a water-containing fluid comprising allowing a water-containing fluid to come into contact with a water absorbent comprising:

(a) a swellable hydrophobic polymer being capable of absorbing a quantity of water which is at least about 10 times the dry weight of said polymer; and (b) an amount of an ionizable surfactant sufficient to form at least a monolayer of said surfactant about said polymer.

BRIEF DESCRIPTION OF THE FIGURES

FIG. 1 schematically illustrates the micellar formation of an anionic surfactant with a hydrophobic gel. Ionic surfactants, such as sodium dodecylsulfate, SDS, are known to form rod-like micelles at high salt concentrations. Missel, P.J. et al., *Solution Behavior of Surfactants*, 1: 373-388, (1982), Mittel, K.L. and Fendler, E.J., edit., Plenum Pub., which is incorporated by reference. Presence of hydrophobic polymers are expected to facilitate the rod-like micellar formation.

Curve A depicts MAPTAC (+) (20 mg). Curve B depicts Acrylic Acid (−) (20 mg). Curve C depicts a mixture of MAPTAC (+) (10 mg) and Acrylic Acid (−).

DESCRIPTION OF TUE PREFERRED EMBODIMENTS

The screening effect inhibits the long range electrostatic interaction between neighboring polymer charge sites due to salt ions intercalating between the sites. The problem is solved either by insulating the charged polymer with a layer of nonpolar medium, or by aligning the charges so closely that the ions cannot intercalate between them.

Figure 1:
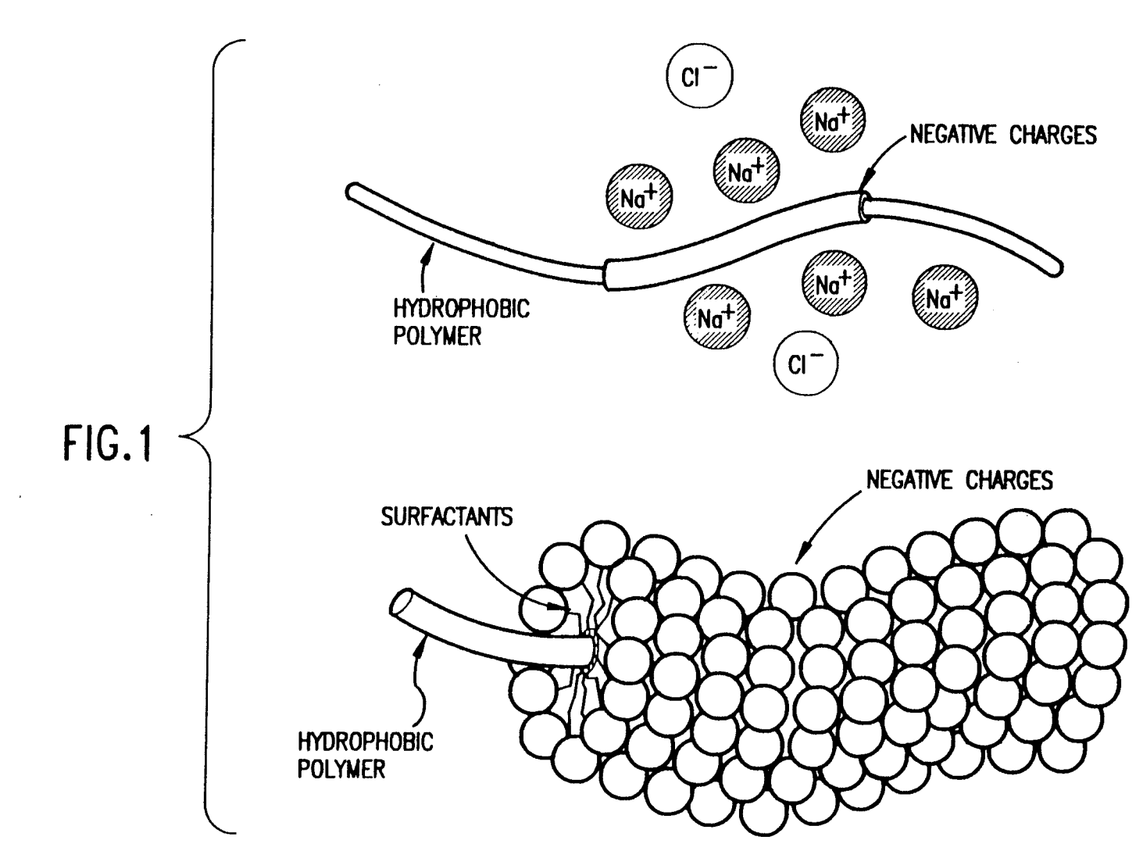

Here we demonstrate an example of the latter scheme, as one embodiment of the present invention, in which a combination of a non-ionic hydrophobic gel and an ionized surfactant was used. The gel/surfactant combination has been shown to have the characteristics of a polyelectrolyte gel. Kokufuta, E. et al., *Proceedings of the 33rd UPAC International Symposium on Macromolecules*, 1.3.9, No. 51 (1990); Inomata, H. et al., *Proc. 4th Gel Symposium*, Polymer Society of Japan 42–43 (1991), which are incorporated by reference. The hydrophobic portion of the surfactant strongly interacts with the polymer chains and forms a thin micellar rod along the polymer chain. Missel, P.J. et al., *Solution Behavior of Surfactants*, 1: 373–388 (1982), Mittel, K.L. and Fendler, E.J., edit., Plenum Pub., which are incorporated by reference. The ionized groups are closely packed in the form of a tube (FIG. 1). The surfactant charges are too close for $Na^+$ and $Cl^-$ ions to come between them, and thus the screening is locally eliminated.

This idea has been successfully tested on the poly(N-isoproplyacrylamide)(NIPA) gel and sodium dodecyl sulfate (SDS) surfactant. The effect of the salt solution was evaluated by determining the phase transition of the gel. Ionized hydrophobic gels, such as an acrylic acid-NIPA copolymer gel, are known to undergo a discontinuous volume phase transition between swollen phase at lower temperatures and collapsed phase at higher temperatures. Hirotsu, S. et al., *Chem. Phys.*, 79: 2554–2558 (1982), which is incorporated by reference. The transition is a result of the competing forces of repulsive electrostatic interaction that act to swell the gel, and attractive forces that tend to shrink the gel. Tanaka, T., *Phys. Rev. Lett.*, 45: 1636–1639 (1980), which is incorporated by reference. The greater the ionization of the gel, the higher the transition temperature is and the larger the volume change is at the transition. Also the volume of the swollen state at low temperatures increases with ionization. When salt is added to the water all these quantities decrease and at physiological salt concentrations they become similar to those of the non-ionized gel. The swelling power of a gel can be quantitatively represented by the transition temperature and by the volume changes at the transition. Ilmaino, F. et al., *Nature*, 349: 400–401 (1991), which is incorporated by reference.

Another embodiment of the present invention is to simply remove the sodium and chloride ions from the solution, so that the ionized group of a gel are not screened. Removals of ions are usually done by ion exchangers. When sodium ions are removed, however, a new set of cations are released that will also screen the charges. Therefore the gel will not retain its superabsorbent power.

Figure 4:
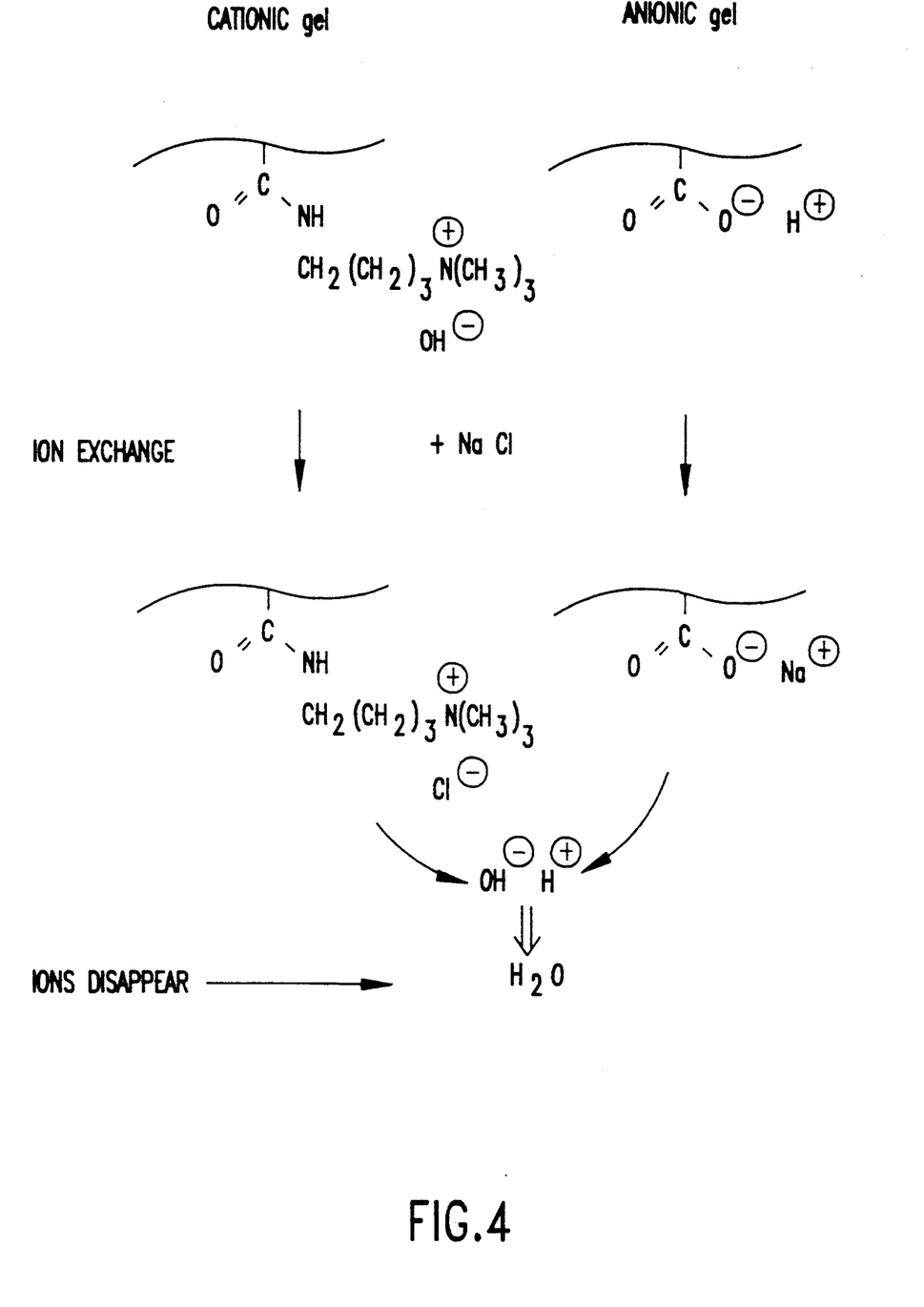
FIG. 4 schematically illustrates that when acrylic acid gel and MAPTACO gels coexist, NaCl in solution is replaced by $H^+$ and $OH^-$ from each gel. These ions are combined to form $H_2O$, and therefore the counter-ion concentrations are drastically reduced. At the same time both gels are fully ionized and swell to their maximum capacities.

This embodiment of the present invention presents a scheme using two different gels, one is cationic and exchanges $Cl^-$ with OH, and the other is anionic and exchanges $Na^+$ with $H^+$ (FIG. 4). When two such gels coexists NaCl in solution is replaced by $H^+$ and $OH^-$ from each gel. The $H^+$ and $OH^-$ ions are combined to form $H_2O$ and therefore the counterion concentrations are drastically reduced. At the same time both gels are fully ionized and swell to their maximum capacities.

The scheme works best for the salt solution volume that has the molar amount of NaCl equal to the exchangeable ionic amounts within the gels. The screening effect will persists if unexchanged sodium and chloride ions remain in the solution.

EXAMPLES

Example 1

The gel was prepared by standard radical polymerization. Hirotsu, S., *Chem. Phys.*, 79: 2554–2558 (1982), which is incorporated by reference. 7.9 g (700 mM) of NIPA (main polymer constituent), 0.133 g of N,N-methylenebisacrylamide (cross-linkers), 240 μl of tetramethyletylenediamine (accelerator), and 40 mg of ammonium persulfate (initiator) were dissolved in 100 μl of water. The solution was degassed and polymerized in capillaries of 100 μm diameter. The gel was cut into a small cylinder of length 1 mm and placed in NaCl solutions of various concentrations. To determine the temperature-dependent volume phase transition characteristics of the gel, pure water and NaCl solutions with and without 2 wt % sodium dodecyl sulfate (SDS) were used. The gel with SDS -was also tested in the presence of urine.

For the NIPANa aclylate gel in pure water, the transition temperature was high (83° C.) and the volume change was large (20 times). In 0.15M salt solution the discontinuous volume transition disappeared and the transition temperature, as defined as the inflection point of the swelling curve, as only 43° C. due to disappearance of the swelling power. The volume at 20° C. was seven times smaller than in the pure water. See FIG. 2a.

When immersed in a 0.15M NaCl solution, the NIPA gel underwent a three fold volume change at 34° C. When 2% SDS was added to the solution, the transition temperature rose to 90° C. and the volume change became 30 fold. The phase behavior of the NIPA/SDS gel was not significantly affected by the addition of NaCl even at 1M NaCl concentration. See FIG. 2b.

Figure 3:
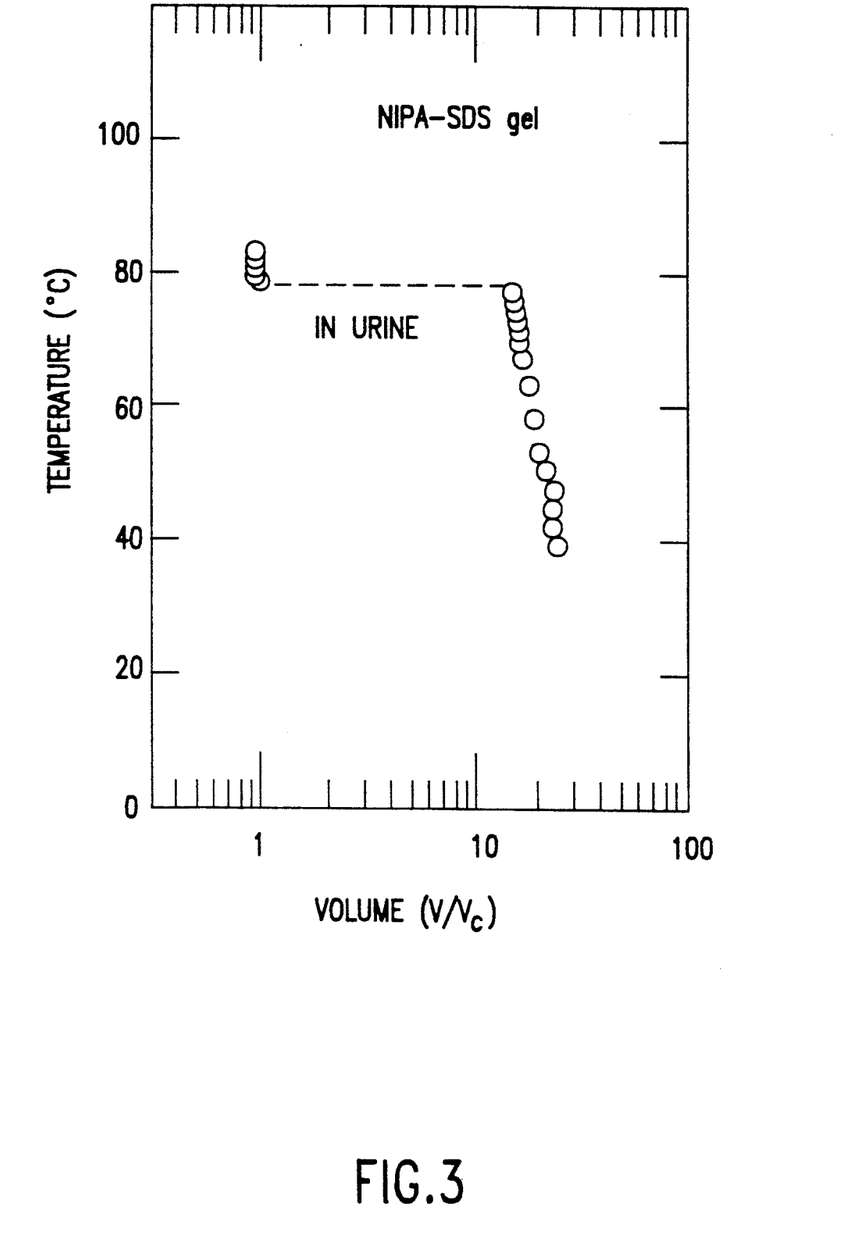
FIG. 3 shows the temperature dependence of the volume of the NIPA/SDS gel in human urine. The solution contains 2 wt % SDS. The swelling curve is similar to that for the gel with SDS in pure water. This indicates that the gel retains the high swelling power in human urine.

Finally, the swelling curve of the NIPA/SDS gel was determined in human urine. No significant change in the swelling of the gel was observed from that in pure water, indicating that the swelling power was indeed preserved under physiological conditions. See FIG. 3.

The SDS absorption to NIPA gel was reversible. It may be washed away by a water or salt solution. For practical purposes it will be necessary to covalently cross-link the surfactants to the polymers.

Example 2 Comparative

Figure 2A:
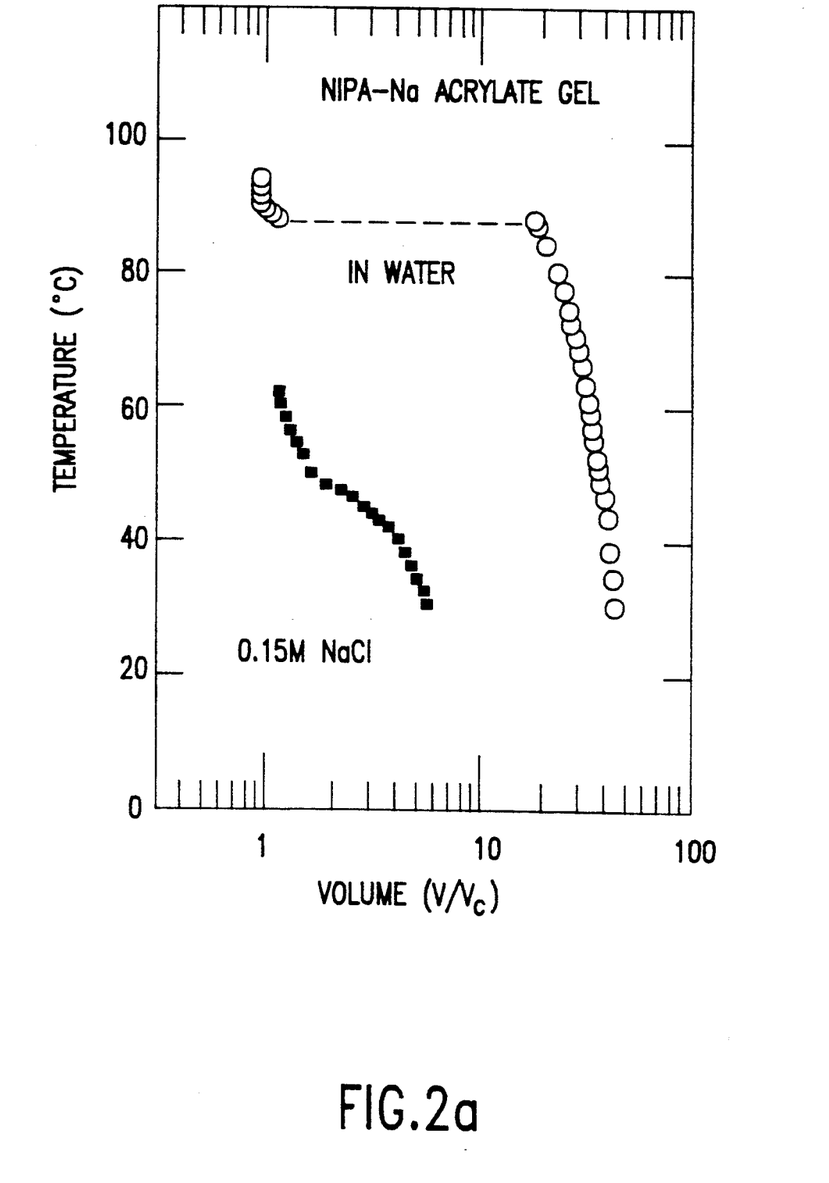
FIG. 2a shows the temperature dependence of the volume of a copolymer gel of poly(N-isopropylacrylamide) (NIPA, 636 mM) and acrylic acid (64 mM, ionizable groups) in the 0.15M NaCl solution. The swelling power in 0.15M NaCl is similar to the non-ionic NIPA gel.
Figure 2B:
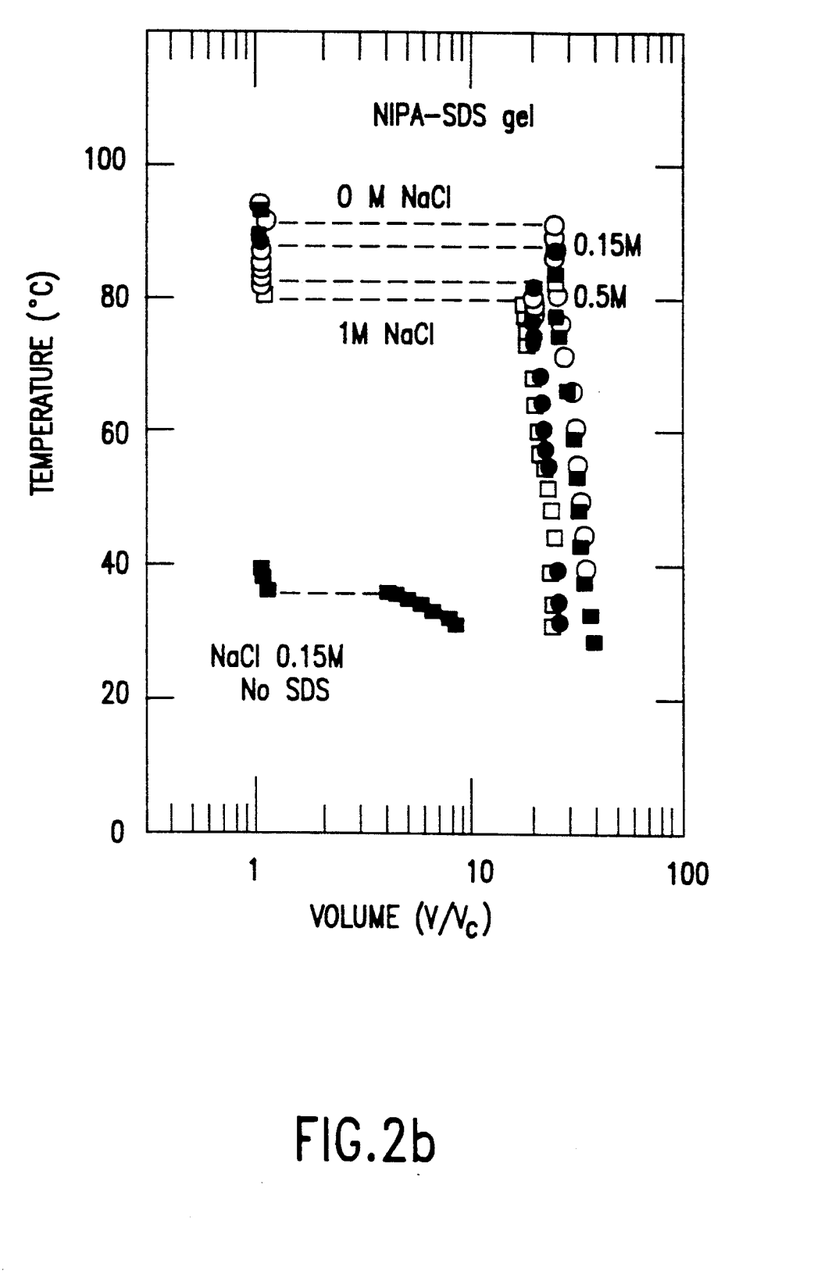
FIG. 2b shows the temperature dependence of the volume of a non-ionic NIPA gel in NaCl solutions of various concentrations. The solution contains 2 wt % SDS. There is no marked changes in the swelling curves, indicating that the gel retains the high swelling power in salt solutions up to 1M concentration of NaCl.

A copolymer gel of 636 mM NIPA and 64 mM sodium acrylate (ionizable group) was also prepared in a similar way as the above NIPA gel of Example 1. The copolymer gel characteristics are shown in FIG. 2a.

Example 3

The combination of pure acrylic acid and methacrylamido-propyltrimethyl-ammonium-hydroxide (MAPTAHO) is prepared as follows. The two gels were separately prepared by standard radical polymerization. Tanaka, T. et al., *Phys. Rev. Lett.*, 45, 1636-1639 (1980), which is incorporated by reference. 5.0 g of acrylic acid (main polymer constituent), 0.133 g of N, N-methylenebisacrylamide (cross-linker), 240 μl of tetramethylethylenediamine (accelerator), and 40 mg of ammonium persulfate (initiator) were dissolved in 100 ml of water. The solution was degassed and polymerized at 60° C. The gel was washed with water, cut into small pieces, and was dried.

A similar preparation method was used to prepare the MAPTAHO gel MAPTAC (Cl⁻form) was used instead of acrylic acid. The gel was washed with 0.01M of NaOH solution to replace Cl⁻ with OH⁻.

Figure 5:
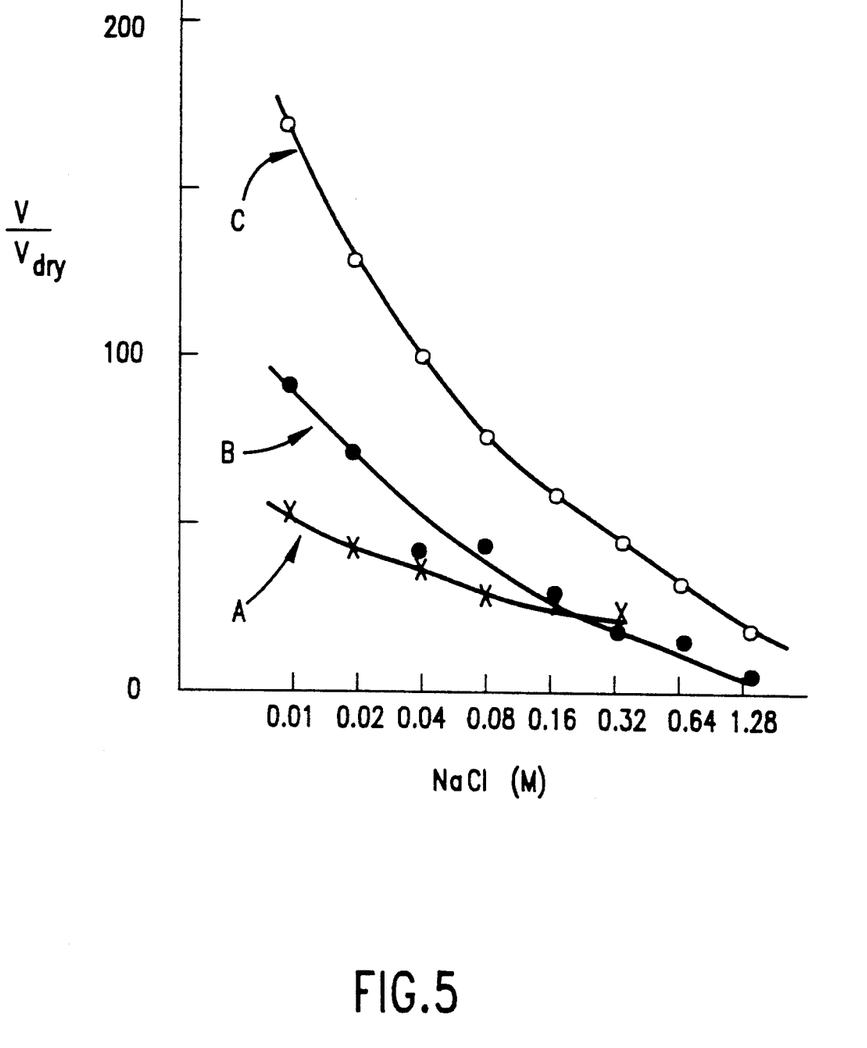
FIG. 5 shows the volumes of three gels, acrylic acid, methacrylamido-propyltrimethyl-ammonium-hydroxide (MAPTAHO), and their mixture, as a function of NaCl concentration when the gels are immersed in solution. The total molar amounts of these gels are the same: 20 mg of acrylic acid, 60 mg of MAPTAHO, and the mixture of 10 mg of acrylic acid and 30 mg of MAPTAHO. The salt concentrations used are 0, 0.015, 0.03, 0.8, 0.15, 0.5, and 1M of NaCl.

We have determined the swelling power of the gel in terms of its volume increase in the presence of salt solutions of progressively increasing salt concentrations, i.e., from 0.0 to 1M NaCl. We have found that the MAPTAHO and the pure acrylic gels separately have a significantly lower swelling power on an equal molar basis than the mixture of MAPTAHO and acrylic acid. See FIG. 5.

The absorbent compositions disclosed can be varied in a number of ways. The description is intended to illustrate the principles and representative compositions that are salt tolerant super absorbents and not to rigidly define the compositions. It is understood that changes and variations can be made therein without departing from the scope of the invention as defined in the following claims.

What is claimed is:
1. A super water absorbent composition comprising:
 (a) a swellable hydrophobic polymer; and
 (b) an amount of an ionizable surfactant sufficient to form at least a monolayer of said surfactant about said polymer, wherein the absorbent composition is capable of absorbing an aqueous solution containing about 1.0M sodium chloride in a quantity such that the weight of the absorbed aqueous solution is at least about 10 times the dry weight of the hydrophobic polymer.

2. The super water absorbent composition of claim 1 in which the temperature-dependent volume phase transition characteristics of the composition consisting of a transition temperature and a volume change at the transition are substantially the same as that which occurs in pure water.

3. The super water absorbent composition of claim 1 in which the ionizable surfactant is anionic, cationic or combinations thereof.

4. The super water absorbent composition of claim 1 in which said surfactant comprises a nonpolar hydrophobic chain to which is attached a polar hydrophilic group.

5. The super water absorbent composition of claim 1 in which said surfactant comprises sodium dodecylsulfate.

6. The super water absorbent composition of claim 5 in which said surfactant is present in an amount ranging from about 1 to about 10 percent by dry weight of said polymer.

7. The super water absorbent composition of claim 1 in which said surfactant comprises dodecyltrimethyl ammonium bromide.

8. The super water absorbent composition of claim 7 in which said surfactant is present in an amount ranging from about 1 to about 10 percent by dry weight of said polymer.

9. The super water absorbent composition of claim 1 in which said ionizable surfactant further comprises a crosslinkable group.

10. The super water absorbent composition of claim 9 in which said ionizable surfactant is crosslinkable by UV light.

11. The super water absorbent composition of claim 10 in which said ionizable surfactant is oleic sulfate.

12. The super water absorbent composition of claim 1 which further comprises a polyacrylamide.

13. The super water absorbent composition of claim 1 in which said polymer comprises poly (N-isopropylacrylamide).

14. The super water absorbent composition of claim 1 which further comprises poly(acrylic acid).

15. The super water absorbent composition of claim 1 which further comprises poly(N-isopropyl-acrylamide-co-acrylic acid).

16. The super water absorbent composition of claim 1 in which said absorbent further comprises a crosslinking agent.

17. The super water absorbent composition of claim 11 in which said crosslinking agent comprises an alkylenebisacrylamide.

18. The super water absorbent composition of claim 12 in which said crosslinking agent is N,N'-methylenebisacrylamide.

19. The super water absorbent composition of claim 1 that is in the form of a partially swollen gel.

20. The super water absorbent composition of claim 1 in which said polymer has functional groups comprising crown ethers.

21. The super water absorbent composition of claim 1 that is capable of retaining its super water absorbing properties and temperature-dependent volume phase transition characteristics when brought into contact with an aqueous solution containing up to about 0.15M sodium chloride.

22. The super water absorbent composition of claim 1 that is capable of retaining its super water absorbing properties and temperature-dependent volume phase transition characteristics when brought into contact with an aqueous solution containing up to about 0.5M sodium chloride.

23. The super water absorbent composition of claim 1 that is capable of retaining its super water properties and temperature-dependent volume phase transition characteristics when brought into contact with an aqueous solution containing up to about 1M sodium chloride.

* * * * *